United States Patent [19]
Ohm

[11] Patent Number: 5,828,813
[45] Date of Patent: Oct. 27, 1998

[54] SIX AXIS FORCE FEEDBACK INPUT DEVICE

[75] Inventor: Timothy Ohm, La Crescenta, Calif.

[73] Assignee: California Institute of Technology, Pasadena, Calif.

[21] Appl. No.: 734,966

[22] Filed: Oct. 23, 1996

Related U.S. Application Data

[63] Continuation-in-part of Ser. No. 525,813, Sep. 7, 1995, Pat. No. 5,710,870.

[51] Int. Cl.$^6$ ..................................................... B25J 15/08
[52] U.S. Cl. ................................................. 395/95; 901/28
[58] Field of Search ................................. 395/95; 901/28

[56] References Cited

U.S. PATENT DOCUMENTS 4,865,376  9/1989  Leaver et al. ............................. 901/15

*Primary Examiner*—George B. Davis
*Attorney, Agent, or Firm*—Michaelson & Wallace

[57] ABSTRACT

The present invention is a low friction, low inertia, six-axis force feedback input device comprising an arm with double-jointed, tendon-driven revolute joints, a decoupled tendon-driven wrist, and a base with encoders and motors. The input device functions as a master robot manipulator of a microsurgical teleoperated robot system including a slave robot manipulator coupled to an amplifier chassis, which is coupled to a control chassis, which is coupled to a workstation with a graphical user interface. The amplifier chassis is coupled to the motors of the master robot manipulator and the control chassis is coupled to the encoders of the master robot manipulator. A force feedback can be applied to the input device and can be generated from the slave robot to enable a user to operate the slave robot via the input device without physically viewing the slave robot. Also, the force feedback can be generated from the workstation to represent fictitious forces to constrain the input device's control of the slave robot to be within imaginary predetermined boundaries.

32 Claims, 10 Drawing Sheets

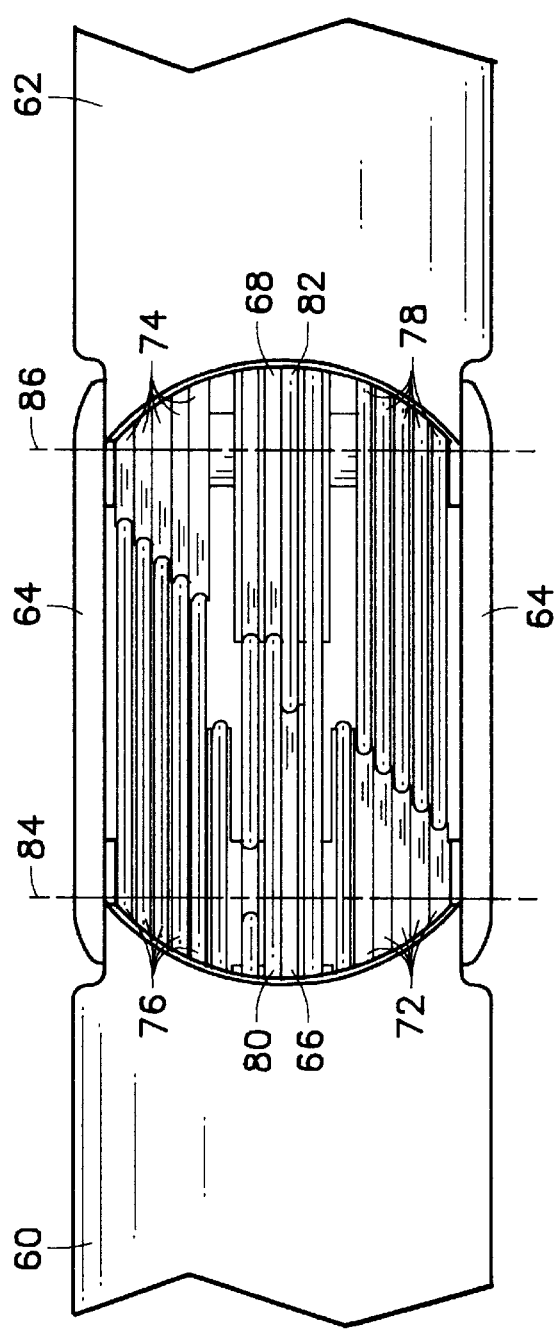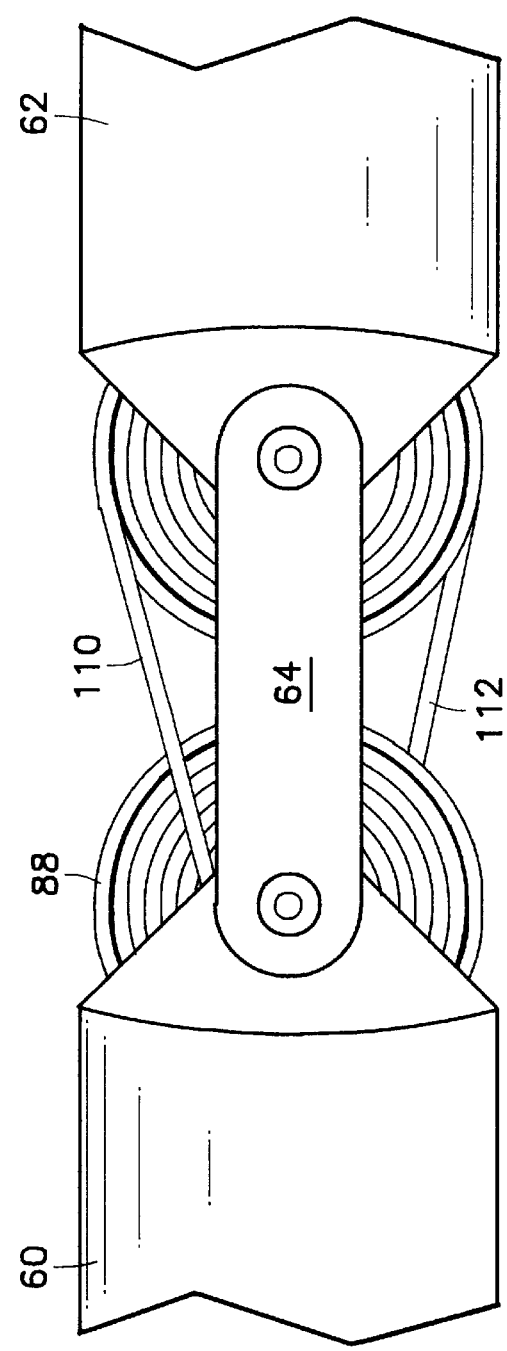
FIG. 4
FIG. 5

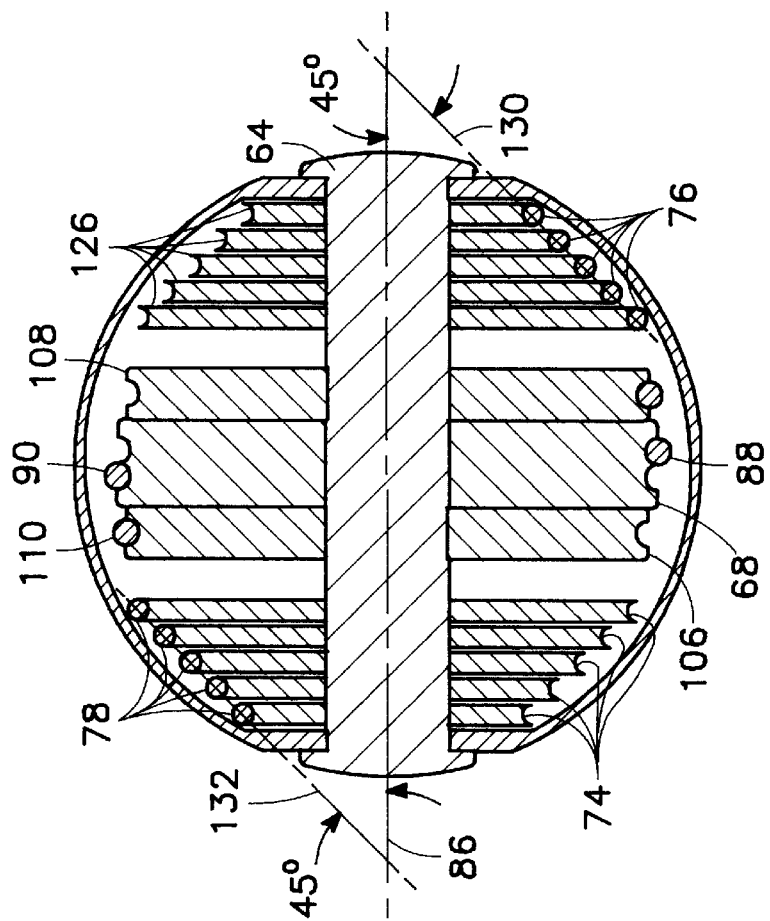
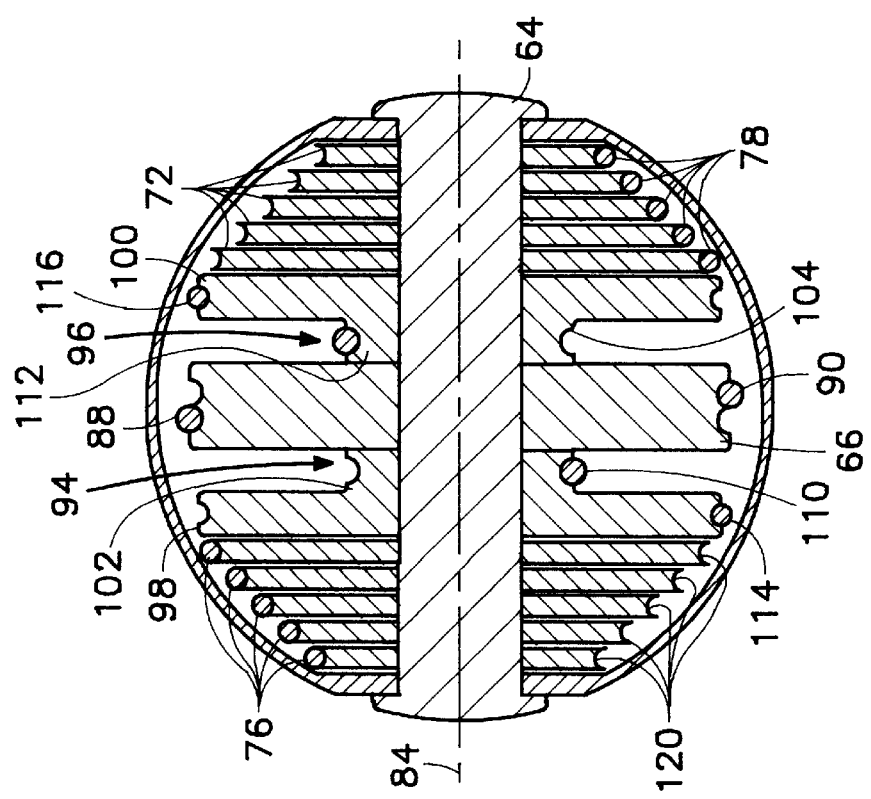
FIG. 7
FIG. 8

SIX AXIS FORCE FEEDBACK INPUT DEVICE

CROSS-REFERENCE TO RELATED APPLICATIONS

This application is a continuation-in-part of application Ser. No. 08/525,813 filed Sep. 7, 1995, U.S. Pat. No. 5,710,870 by Ohm et al. entitled "A DECOUPLED SIX DEGREE-OF-FREEDOM ROBOT MANIPULATOR".

BACKGROUND OF THE INVENTION

Origin of the Invention

The invention described herein was made in the performance of work under a NASA contract, and is subject to the provisions of Public Law 96-517 (35 USC 202) in which the contractor has elected to retain title.

FIELD OF THE INVENTION

The present invention relates in general to robot manipulators and in particular to a low friction, low inertia, six-axis force feedback input device with double-jointed, tendon-driven revolute joints for robot assisted microsurgery.

RELATED ART

Robotic devices are commonly used in factory based environments to complete tasks such as placing parts, welding, spray painting, etc. Examples of robotic systems include U.S. Pat. No. 4,911,033, issued to Rosheim et al., and U.S. Pat. Nos. 4,729,253, 4,723,460, and 4,686,866, issued to Rosheim.

Although these systems are used for a variety of tasks, the Rosheim et al. and Rosheim robotic systems lack important features. For instance, they do not have completely mechanically decoupled axes with passed actuation for transferring actuation through one joint in order to actuate another joint, without affecting the motion of any other joints. In addition, the Rosheim et al. and Rosheim robotic systems are large and bulky and cannot effectively perform small scale tasks, such as microsurgical operations. Also, the Rosheim et al. and Rosheim robotic systems are not tendon-driven systems, and thus, do not have low or zero backlash, which is desirable for microsurgical operations.

Recently, other robotic devices have been used in medical environments to perform surgical operations. Some of these devices include micro-robots having miniaturized end effectors with tendon-driven joints. However, current tendon-driven robot manipulators for small scale microsurgical manipulation suffer from inefficient coupling between joints, inadequate stiffness, packaging problems associated with achieving constant cable path lengths, and activation of multiple joints. In addition, these microsurgical robotic systems do not have force-feedback capabilities.

Also, in many robotic geartrain applications, such as high precision microsurgical operations, zero backlash is desired. Conventional approaches use various antibacklash components, such as high precision connectors and antibacklash gears, to eliminate backlash in each stage of the geartrain independently. These antibacklash gears are used in each stage and are stacked until the desired gear ratio is achieved. Nevertheless, these conventional approaches are difficult to implement since each stage of the geartrain ideally requires a unique preload (initial loading of the geartrain to snugly 'set' the gears within each other) value. Moreover, preloading is typically tedious and difficult to readjust, if required.

Therefore, what is needed is an input device functioning as a master robot to control a slave robot with passed actuation capabilities, zero backlash, high dexterity, at least six degrees of freedom with all six axes being completely mechanically decoupled, low inertia, low frictional aspects, and force-feedback capabilities.

Whatever the merits of the above mentioned systems and methods, they do not achieve the benefits of the present invention.

SUMMARY OF THE INVENTION

To overcome the limitations in the prior art described above, and to overcome other limitations that will become apparent upon reading and understanding the present specification, the present invention is a six-axis force feedback input device. The input device comprises an arm with double-jointed, tendon-driven revolute joints, a decoupled tendon-driven wrist with a force/torque sensor, and a base with encoders and motors.

A force feedback can be applied to the input deivce for providing feedback to an operator of the input device. The force feedback can be generated from a slave robot, which the input device controls. Also, the force feedback can be generated from an external device, such as a programmed processor, to produce fictitious forces on the input device. The fictitious forces can represent desired boundaries to constrain the slave robot within.

The input device functions as a master robot manipulator in a microsurgical teleoperated robot system. The overall system architecture includes a slave robot manipulator coupled to an amplifier chassis. The amplifier chassis is coupled to a control chassis which is coupled to a workstation with a graphical user interface. Also, the amplifier chassis is coupled to the motors of the master robot manipulator and the control chassis is coupled to the encoders of the master robot manipulator. Components of the teleoperated robot system are categorized into a mechanical sub-system, an electronics sub-system, a servo-control sub-system, and a high-level software control sub-system.

The master robot manipulator has six degrees of freedom and includes a torso connected to the actuator base (which rotates about a housing canister). The torso is also rotatably coupled to an arm. The arm comprises two double-jointed robot joints decoupled from each other and a wrist connected to an end effector. The double-jointed robot joints include an input link having a first keying drive component and an output link coupled to the input link and having a second keying drive component. The first keying drive component is constrained to rotate with respect to the second keying drive component, thereby defining an instantaneous center of rotation.

In addition, each double-jointed decoupled joint has a first passing drive component rotatable on the input link and coupled to the actuator of the actuator base. A second passing drive component rotatable on the output link is coupled to the first passing drive component. The first passing drive component rotates with respect to the second passing drive component about the instantaneous center of rotation. The pair of passing drive components are kinematically linked to the keying drive component through the instantaneous center of rotation so that each passing drive component of each joint is completely mechanically decoupled from the particular joint's motion. Further, any number of pairs of passing drive components can be used with each decoupled joint as long respective pairs of passing drive components rotate with respect to each other about the instantaneous center of rotation. Moreover, each joint can have an actuation drive component for actuating the particular joint.

The wrist is connected to the end effector and has a tendon-driven system with zero backlash in pitch, yaw, and roll axes. The wrist utilizes a universal drive component system with dual bearing rings for decoupling the pitch and yaw axes.

Features of the teleoperated microsurgical robot of the present invention include double-jointed robot joints, at least six degrees of freedom with all six axes completely mechanically decoupled, decoupled passed actuation, zero backlash in the wrist, and force-feedback capabilities. Advantages of the teleoperated microsurgical robot of the present invention is that it is extremely sensitive and small, has high dexterity, has low inertia, and has low frictional aspects.

The foregoing and still further features and advantages of the present invention as well as a more complete understanding thereof will be made apparent from a study of the following detailed description of the invention in connection with the accompanying drawings and appended claims.

BRIEF DESCRIPTION OF THE DRAWINGS

Referring now to the drawings in which like reference numbers represent corresponding parts throughout:

FIG. 4 illustrates a top view of one embodiment of the decoupled joints with cable driven actuation;

FIG. 5 illustrates a side view of FIG. 4;

FIG. 7 illustrates a cross sectional side view of the input link of FIG. 4;

FIG. 8 illustrates a cross sectional side view of the output link of FIG. 4;

DETAILED DESCRIPTION OF THE PREFERRED EMBODIMENT

In the following description of the preferred embodiment, reference is made to the accompanying drawings which form a part hereof, and in which is shown by way of illustration a specific embodiment in which the invention may be practiced. It is to be understood that other embodiments may be utilized and structural changes may be made without departing from the scope of the present invention.

INPUT DEVICE OVERVIEW

Figure 1:
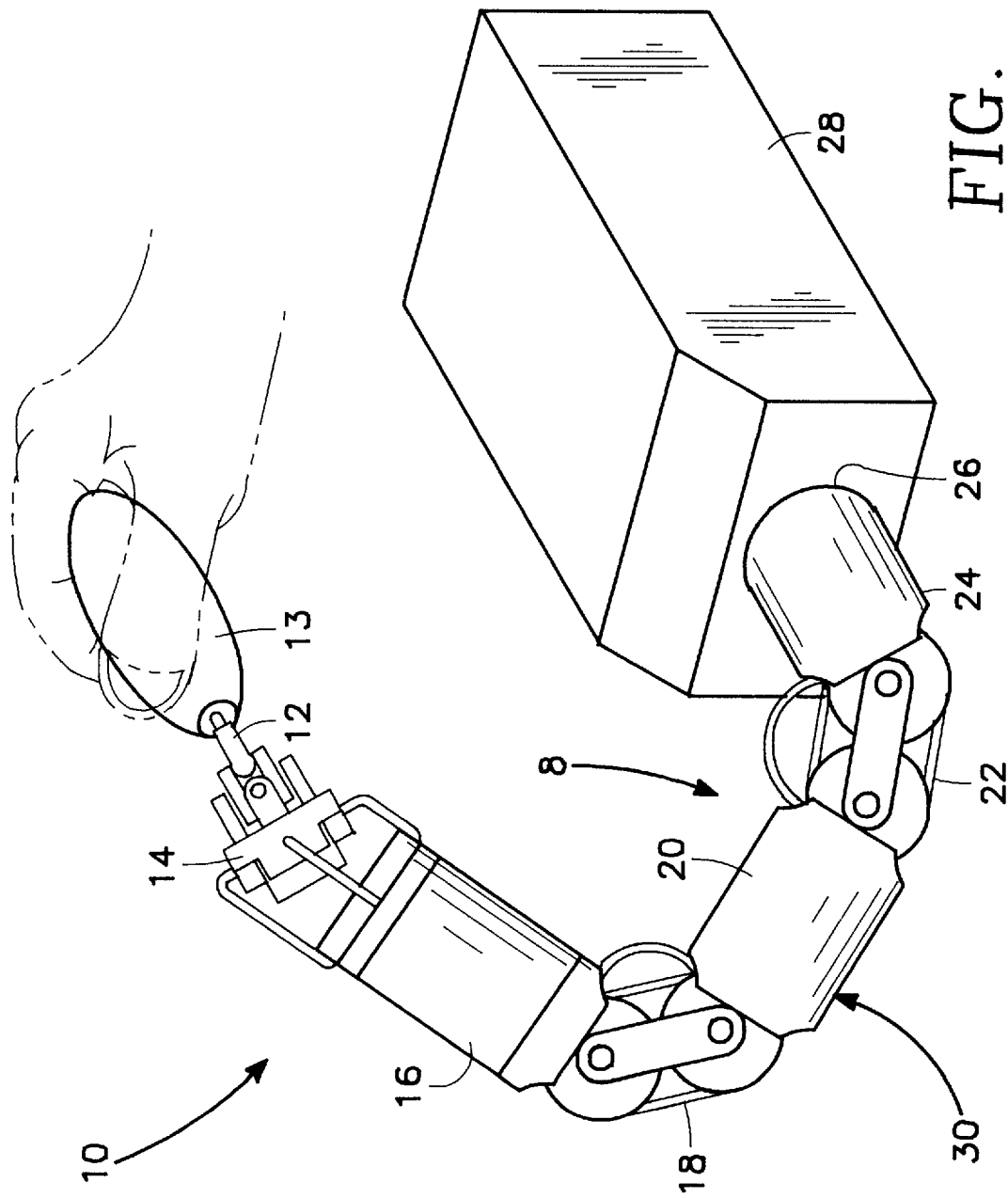
FIG. 1 illustrates an overall view of the input device of the present invention.

FIG. 1 illustrates an overall view of the input device 8 of the present invention. In the preferred embodiment, the input device 8 functions as a master robot manipulator for a microsurgical teleoperated robot system for controlling the movement of a slave robot manipulator (described in detail below in FIG. 16).

The input device 8 or master robot manipulator comprises an arm 10 coupled to a wrist 14. The wrist 14 is coupled to a six-axis force/torque sensor 12 which is coupled to a stylus 13 located outboard of the sensor 12. The wrist 14 provides an intersecting axis for pitch, yaw, and roll and is coupled to a forearm 16 which is coupled to a doubled-jointed elbow joint 18 for connecting an upper arm 20 to the forearm 16. The upper arm 20 is coupled to a double-jointed shoulder joint 22 for connecting a shoulder 24 to the upper arm 20. The shoulder 24 is coupled to a torso joint 26 which is coupled to an actuator base 28.

The actuator base 28 contains an antibacklash mechanism and electrical and mechanical components for receiving input from the input device 8 and transmitting the input for teleoperation. The electrical and mechanical components receive feedback from an external device, such as a programmable processor or a torque sensor located on the slave robot of FIG. 16, which is controlled by the input device 8. The electrical and mechanical components transmit the feedback to the input device 8.

The forearm 16, upper arm 20, and shoulder 24 all preferably have housings in the form of cylindrical casings 30. The torso joint 26 is rotatable relative to the actuator base 28. The wrist joint 12 has three degrees of freedom and each joint (elbow 18, shoulder 22, and torso 26) has one degree of freedom.

In addition, the input device 8, functioning as a master robot 8, has indexing capabilities. For example, during operation of the system, if the master robot 8 reaches its physical end of travel or its range of motion has reached its boundaries, but the slave robot of FIG. 16 requires further movement, the master robot 8 can be temporarily deactivated, relocated within its boundaries, and then reactivated to provide the additional movement required by the slave. Thus, the master robot 8, operating in a limited space area, can control the movement of the slave robot within an infinite area, restricted only by the physical limitations of the system.

The double-jointed robot joints 18 and 22 and the wrist joint 14 can be used in large automated environments, as well as micro automated environments, including microsurgical environments. The double-jointed robot joints 18 and 22 will be discussed in detail below in FIGS. 2–10, one robot wrist 12 will be discussed in detail below in FIG. 11, the base 28 and its components will be discussed in detail below in FIGS. 12–13, one antibacklash system will be discussed in detail below in FIGS. 14–15, and the robot manipulator will be described in detail below in FIG. 16. Although the robot manipulator can be used in numerous environments, the preferred embodiment involves the use of the robot manipulator in a microsurgical environment.

DOUBLE-JOINTED, DECOUPLED JOINTS

Figure 2:
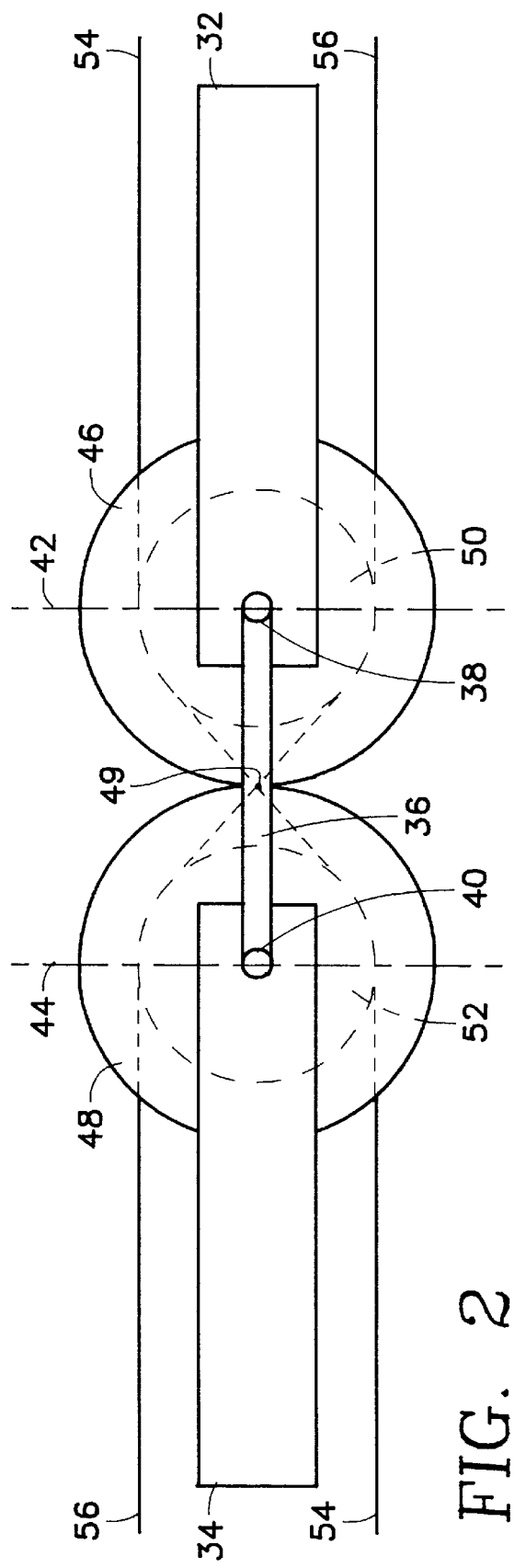
FIG. 2 illustrates a side view of the general decoupled robot joints of the present invention.

FIG. 2 is a side view and general overview of a double-jointed, decoupled robot joint of the present invention. FIG.

3 illustrates a top view of FIG. 2. The double-jointed robot joint couples sections of the robot 8 of FIG. 1 together. Each double-jointed robot joint can have internal actuators, such as an internal actuation pulley/cable system (described in detail in FIGS. 4–8) coupled to external motors located at the actuator base 28 of FIG. 1 or internal motors in each joint (not shown) for actuating the particular joint or other joints of the robot.

Figure 3:
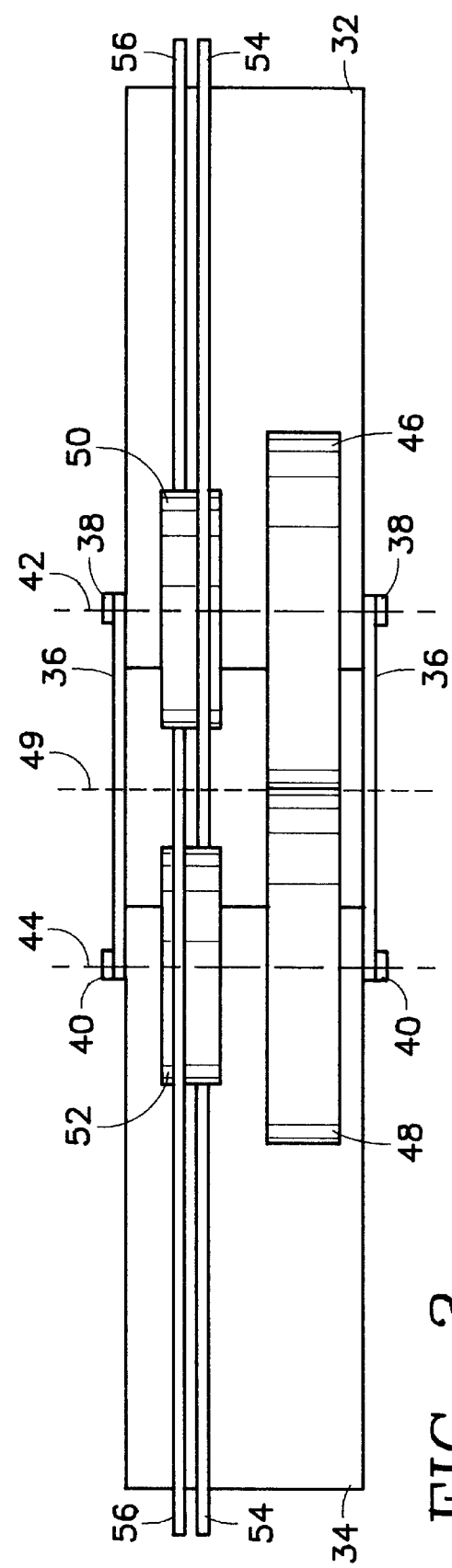
FIG. 3 illustrates a top view of FIG. 2.

The double-jointed robot joint of FIGS. 2 and 3 includes an input link 32 and an output link 34. The input link 32 is on the near side of the actuator base 28 while the output link 34 is on the far side of the actuator base 28 and is moveable relative to the input link 32. The input and output links 32, 34 are attached to each other via a pair of hinged side struts 36. The links 32, 34 pivot about pivot points 38 and 40 at the input link 32 and output link 34, respectively. These pivot points 38 and 40 define an input axis 42 and output axis 44, respectively.

An input keying drive component 46 and an output keying drive component 48 are centered on each respective hinged axis or pivot point 38 and 40 and are attached to each respective link 32 and 34 so that they are constrained to rotate with respect to each other. This constrained rotation between the input keying drive component 46 and the output keying drive component 48 defines an instantaneous center of rotation 49 between the two keying drive components 46 and 48. The keying drive components 46 and 48 can be fixed spur gears which mesh together or they can be fixed pulleys with wound cables as described in detail below.

In addition, each joint has an input passing drive component 50 rotatable about the pivot point 38 of the input link 32. The input passing drive component 50 is coupled to an actuator (not shown) at the actuator base 28 of FIG. 1 and to an output passing drive component 52. The output passing drive component 52 is rotatable about the pivot point 40 of the output link 34. The passing drive components 50 and 52 can be a spur gear system or a pulley system. In a pulley system, respective passing cables passing through each respective passing drive component would be included.

For example, a first passing cable 54, originating from another passing drive component in another joint or from the actuator base 28 of FIG. 1, travels from the input link 32, around the top of the input passing pulley 50, through the instantaneous center of rotation 49, and then around the bottom of the output passing pulley 52. A second passing cable 56, originating from the same location as the first passing cable 54, travels from the input link 32, around the bottom of the input passing pulley 50, through the instantaneous center of rotation 49, and then around the top of the output passing pulley 52.

This arrangement allows the input passing drive component 50 to rotate with respect to the output passing drive component 52 about the same instantaneous center of rotation 49 defined by the input and output keying drive components 46 and 48. Since the pair of passing drive components rotate about the same instantaneous center of rotation 49 as the keying drive components 46 and 48, the passing drive components 50 and 52 are kinematically decoupled from the joint's motion. This decoupling configuration allows the passing drive components 50 and 52 to actuate movement in other joints without affecting the motion of the particular joint.

Further, any number of pairs of passing drive components can be used with each joint as long as coupled pairs of passing drive components (input and output) rotate with respect to each other about the same instantaneous center of rotation defined by the keying drive components.

DOUBLE-JOINTED TENDON-DRIVEN DECOUPLED JOINTS

FIGS. 4–10 show a tendon-driven system of one embodiment of the double-jointed decoupled robot joints. FIG. 4 is a top view and FIG. 5 is side view of tendon-driven double-jointed decoupled robot joints. The joint of FIG. 4 is structurally similar to the joint of FIGS. 2 and 3 and includes an input link 60, an output link 62, hinged side struts 64, an input keying drive component 66, an output keying drive component 68, an instantaneous center of rotation 70 (shown in FIG. 6), input passing drive components 72, output passing drive components 74, and corresponding passing cables 76 and 78, respectively.

The functions of each element above has the same or similar functions as the related elements of FIGS. 2 and 3. However, the embodiment of FIGS. 4–10 is different in that it is a cable or tendon-driven system and further includes an actuation mechanism. Since the embodiment of FIGS. 4–10 is a cable or tendon-driven robot, the keying drive components 66 and 68 are pulleys with corresponding cables 80 and 82, respectively, which can be stainless steel cables. Also, FIGS. 4–10 further include actuation pulleys and cables within the particular joint for actuating the joint.

The input keying pulley 66 is fixed to the input link 60 and the output keying pulley 68 is fixed to the output link 62 on respective input and output axes 84 and 86. The input axis 84 is defined by a pivot point of the input keying pulley 66 on the input link 60. An output axis 86 is the counterpart to the input axis 84 and is defined by a pivot point of the output keying pulley 68 on the output link 62.

Figure 6:
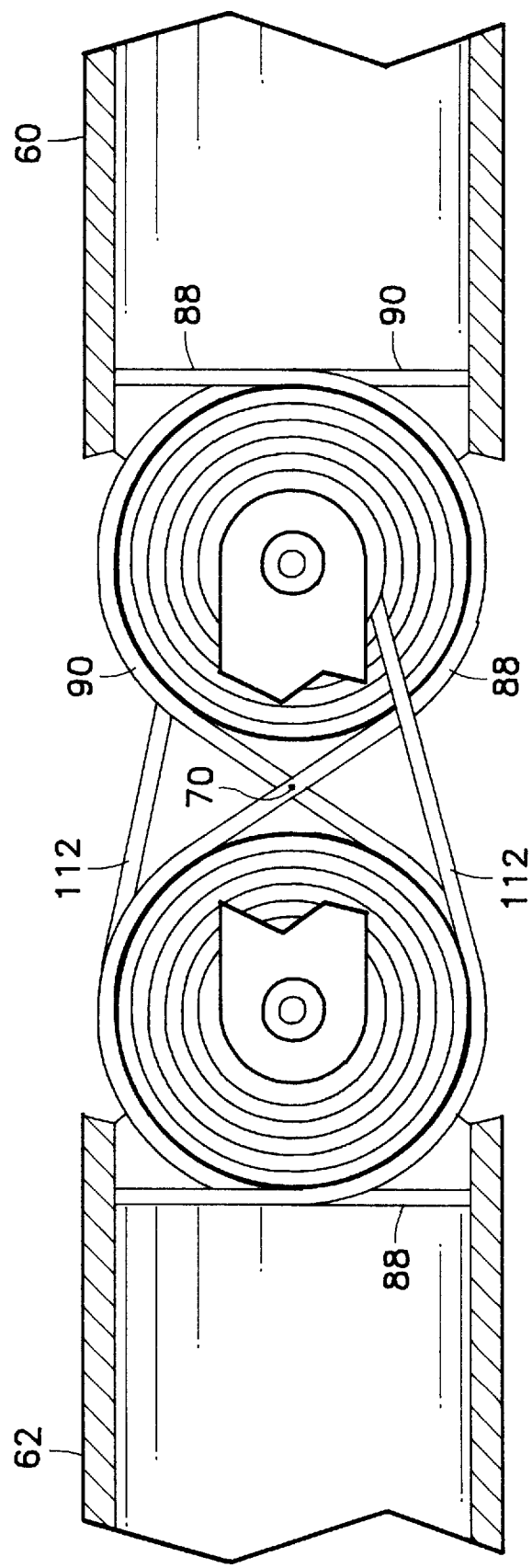
FIG. 6 illustrates a cut-away side view of FIG. 5.

Referring to FIG. 6, two keying cables 88 and 90 are connected to the input link 60 and the output link 62, respectively. The keying cables 88 and 90 can also be connected directly to the keying pulleys 66 and 68, respectively. The first keying cable 88 is attached to a bottom portion of the input link 60 and winds around a top side of the input keying pulley 66, crosses to the output keying pulley 68, winds around a bottom side of the output keying pulley 68, and terminates on a top portion of the output link 62.

The second keying cable 90 is attached to a top portion of the input link 60 and winds around a bottom side of the input keying pulley 66, crosses to the output keying pulley 68, winds around a top side of the output keying pulley 68, and terminates on a bottom portion of the output link 62. The second keying cable 90 traverses a mirrored path of the first keying cable 88. If the cables are stainless steel, the cables 88 and 90 can be terminated with solder joints or crimp terminations. However, soldered terminations are preferred because they are easy to install, take up very little space, and do not inflict an initial stress concentration in the cable, assuming the solder joint is not flexed.

The keying pulleys are constrained to respective links similar to the keying drive component arrangement of FIGS. 2 and 3. Also, the keying pulleys 66 and 68 preferably have the same diameter, but this is not necessary. One feature of the present invention is that the keying cables 88 and 90 cross one another between the keying pulleys 66 and 68 as shown in FIG. 6 to define the instantaneous center of rotation 70. The identical effect of having an instantaneous center of rotation can be achieved with spur gears which mesh together, in a similar manner as the keying drive components 46 and 48 of FIGS. 2 and 3. Although, keying spur gears would introduce backlash into the robot manipulator, backlash can be prevented in the tendon-driven system by a standard single stage antibacklash system or in accordance with the antibacklash system described in detail in FIGS. 14–15. Thus, the present invention is preferably a tendon-driven system consisting of keying cables 88 and 90 and keying pulleys 66 and 68 instead of spur gears.

Figure 9:
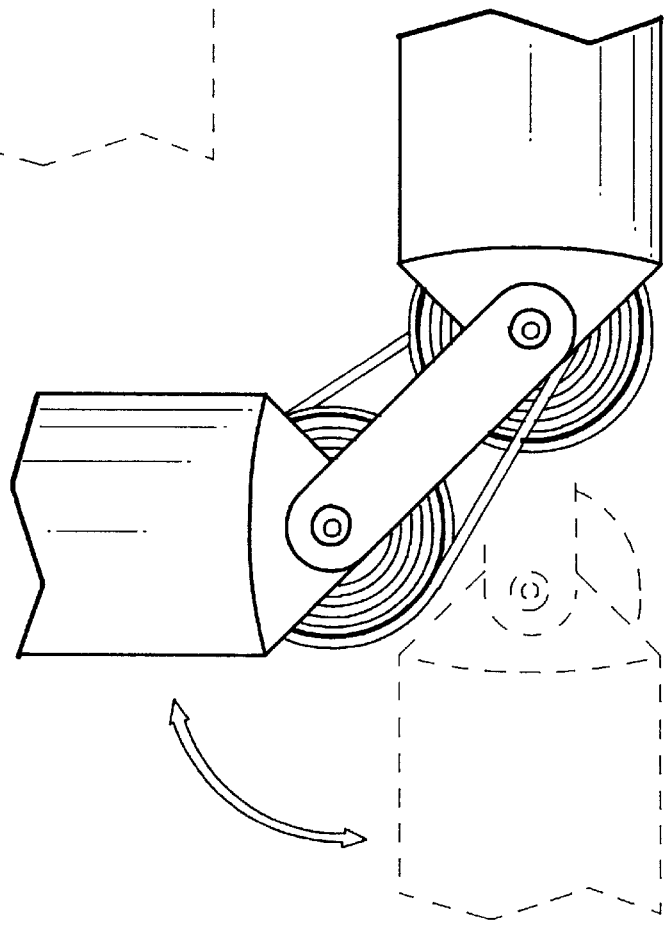
FIG. 9 illustrates a 90 degree deflection of the robot arm connected to the decoupled joint of the present invention.

Each double-jointed robot joint has one degree of freedom. Each joint's rotation is dependant on the ratio of the keying pulleys' 66 and 68 diameters. For example, if both keying pulleys 66 and 68 have the same diameter, the angle that the output link 62 is moved relative to the input link 60 will be exactly twice the angle between the side struts 64 and each link 60 and 62. In other words, if the output link 62 is rotated 90° to the input link 60, the side struts 64 will rotate 45° to each link 60 and 62, as shown in FIG. 9. Likewise, the output link 62 can rotate up to 180° at which point the side struts 64 will be at 90° to each link 60 and 62, as shown in FIG. 10.

Figure 10:
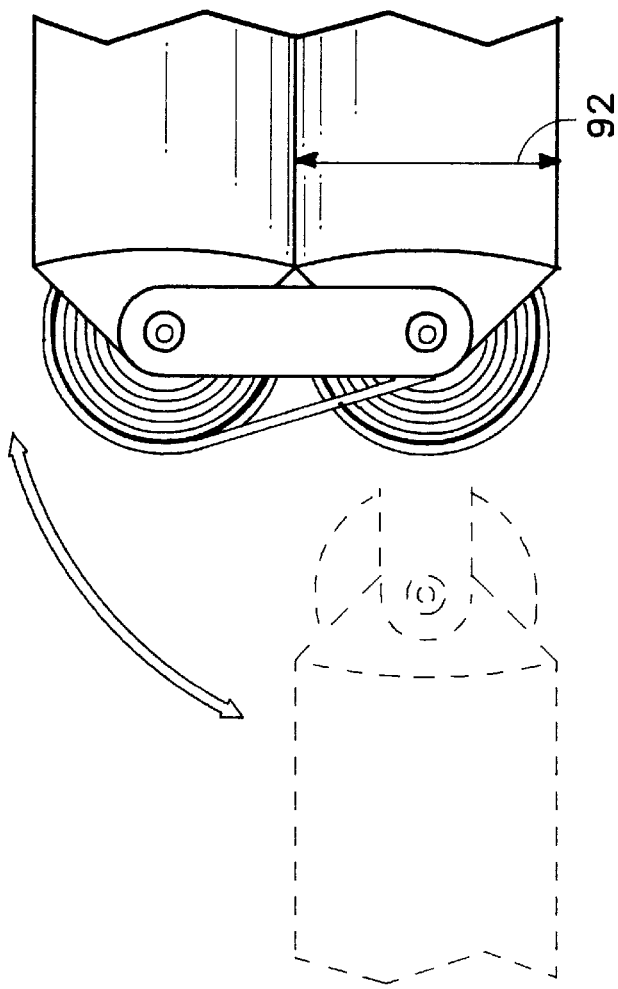
FIG. 10 illustrates a 180 degree deflection of the robot arm connected to the decoupled joint of the present invention.

In order to achieve the maximum 180° rotation, the distance between the input and output axes must be at least equal or greater than an effective diameter 92 of each links 60 and 62, as shown in FIG. 10. It is important to note that the 180° range of motion is bidirectional, thus the full range of joint motion is 360°. Alternatively, if the keying pulleys 66 and 68 have different diameters, other kinematic relationships can be achieved between the input link 60, output link 62, and side struts 64 without affecting other features of the robot.

FIGS. 7 and 8 are cross-sectional views through the input and output axes, respectively. The joint can be actuated by two input dual actuation pulleys 94 and 96. Each input dual actuation pulley 94 and 96 includes transmission pulleys 98 and 100 and connecting pulleys 102 and 104, respectively. The two input dual actuation pulleys 94 and 96 sandwich the input keying pulley 66 on the input axis 84 as shown in FIG. 7. The actuation pulleys 94 and 96 rotate independently of the input keying pulley 66.

Also, two output actuation pulleys 106 and 108 sandwich the output keying pulley 68 on the output axis 86 as shown in FIG. 8. Referring to both FIGS. 7 and 8, each of the connecting pulleys 102 and 104 have corresponding actuation cables 110 and 112 terminated to it. Also, the transmission pulleys 98 and 100 have transmission cables 114 and 116 coupled to the actuator base for actuating the pulleys 94 and 96.

Referring to FIGS. 6–8, the first actuation cable 110 can be terminated to a top side of the connecting pulley 102 of the first input actuation pulley 94 and the second actuation cable 112 can be terminated to a bottom side of the connecting pulley 104 of the second input actuation pulley 96. The first actuation cable 110 travels from the first input actuation pulley 94, winds around a top side of the first output actuation pulley 106, and terminates to a bottom side of the output link 62. The second actuation cable 112 travels from the second input actuation pulley 96, winds around a bottom side of the second output actuation pulley 108, and terminates to a top side of the output link 62. Connecting pulleys 102 and 104 can have the same diameters of actuation pulleys 106 and 108, but this is not necessary. The transmission cables 114 and 116 are coupled to the transmission pulleys 98 and 100 of the input actuation pulleys 94 and 96, respectively, to actuate the output actuation pulleys 106 and 108 through the connecting pulleys 102 and 104 via the actuation cables 110 and 112.

Motors typically operate at high speeds with low torque. However, actuation of the robot joints by motors located at the actuator base typically requires the motor to have low speed with high torque. Gear reduction at the joints resolves this problem by reducing a motor's high speed with low torque to low speed with high torque. The actuation pulleys 106 and 108 can incorporate gear reduction at the joints. For example, if the connecting pulleys 102 and 104 of the input actuation pulleys 94 and 96 have the same diameters, and the output actuation pulleys 106 and 108 have the same diameters, and the connecting pulleys 102 and 104 have different diameters from the output actuation pulleys 106 and 108, a resultant gear reduction ratio for the particular joint will be created.

The resultant gear reduction ratio between the input actuation pulleys 94 and 96 and the output actuation pulleys 106 and 108 is given by:

$$\text{RATIO} = 1/2(1 + d_o/d_i)$$

where $d_o$ is the diameter of the output actuation pulleys 106 and 108 and $d_i$ is the diameter of the connecting pulleys 102 and 104 of the input actuation pulleys 94 and 96. This relationship also assumes that both keying pulleys 66 and 68 have the same diameter. Therefore, if the ratio of the diameters of the output actuation pulleys 106 and 108 to the diameters of the connecting pulleys 102 and 104 of the input actuation pulley is 3:1, the resultant gear ratio for the joint will be 2:1 (the output actuation pulley revolves once for every two revolutions of the input actuation pulley).

Also, gear reduction in close proximity to the joint increases stiffness. Typically, stiffness of a tendon-driven mechanism is directly related to the spring constant of the cable or tendon. Thus, high stiffness is achieved by a high spring constant. In addition, the spring constant is inversely proportional to the cable or tendon length. Hence, short cable paths will yield a high spring constant which in turn produces high stiffness. Relatively high stiffness can be achieved with relatively larger diameter cables or tendons.

A resultant gear reduction ratio of 2:1 will produce a short actuation cable length and relatively high stiffness in the transmission cables 114 and 116. The stiffness is related to the resultant gear ratio by a factor of the resultant gear ratio squared. Thus, the diameter of the transmission cables 114 and 116 can be small, thereby enabling small bend radii and more compact packaging.

Similar to the keying drive components of FIGS. 2 and 3, the actuation pulleys/cables can be a spur gear arrangement which would further increase stiffness. However, unlike the keying drive components 48 and 50 of FIGS. 2 and 3, the use of spur gears with dual transmission path cables 114 and 116 (two transmission paths from the actuator) for the actuation pulleys/cables would not induce backlash into the robot manipulator system. This is because the dual transmission paths are tied together at the actuator of the actuator base of FIG. 1 and the output link only. For example, as a result of the actuation pulley arrangement, the tension in the transmission paths defined by the transmission cables 114 and 116 will automatically preload the actuation cables 110 and 112. Further, if the actuation cables 110 and 112 were replaced with a spur gear train, preloading would likewise occur due to this dual transmission path arrangement.

Referring to FIGS. 4, 7, and 8, the joint of the robot manipulator of the present invention also includes an idler pulley/passing cable system. Passing cables 76 and 78 of passing pulleys 72 and 74 pass through a particular joint to actuate other joints of the robot manipulator, thereby mechanically decoupling the particular joint's motion from the other joints' motion. The passing cables 76 and 78 pass through the joint over input idler pulleys 120 and output 126 idler pulleys. The input idler pulleys 72 and 120 and output idler pulleys 74 and 126 rotate freely about the input axis 84 and output axis 86, respectively. The robot can have an unlimited number of idler pulleys and corresponding passing cables.

In order effectuate complete decoupling from the particular joint's motion to other joints' motion, two constraints must be met. First, for a given passing cable 78, corresponding input 72 and output 74 idler pulleys must have the same diameter ratio as that of the input 66 and output 68 keying pulleys, respectively. For example, if the keying pulleys 66 and 68 have equal diameters (1:1 ratio), the idler pulleys 72 and 74 for a corresponding passing cable 78 must have equal diameters (1:1 ratio), or coupling will occur. The absolute size of the idler pulleys 72 and 74 have no consequence.

The second constraint is that the passing cables 78 must follow the same path as the keying cables 88 and 90 and define the same instantaneous center of rotation 70 as the keying cables 88 and 90. Namely, the passing cables 78 must cross from the idler pulleys 72 on input axis 84 to the idler pulleys 74 on the output axis 86 at the same location the keying cables 88 and 90 cross. As a result, as the joint rotates, the amount of passing cable 78 that is wound onto one idler pulley 72 on the input axis 84 equals the amount of passing cable 78 that is unwound off the idler pulley 74 on the output axis 86.

Also, since the keying pulleys 66 and 68 do not rotate relative to their corresponding links 60 and 62, and the passing cables 78 are cabled via the same scheme as the keying cables 88 and 90, the idler pulleys 72 and 74 are stationary relative to the links 60 and 62. This produces complete decoupling of the joint and the passing cables 78. Further, there is no restriction (other than physical packaging) to the amount of passing cables 78 that can be passed through a particular joint.

In addition, the passing cables 78 path lengths are constant throughout the entire range of travel. Depending on the idler pulley 72 and 74 diameters, it may be necessary to confine the passing cables 78 to prevent lifting off their corresponding idler pulleys 72 and 74. Confinement can be accomplished by wrapping the passing cables 78 completely around the corresponding idler pulleys 72 and 74, or by adding idler pulleys (not shown) inside the links 60 and 62.

If adjacent joints are to be moved perpendicular to one another (the output link of one joint attaches to the input link of another joint such that the resulting output and input axes are perpendicular), two additional constraints on the passing cables 78 are necessary. The first constraint is that two sets of independent idler pulleys, each consisting of an input idler pulley and an output idler pulley, are needed for each path of cable. The second constraint is that the passing cables 78 must be arranged in such a way that they will align to idler pulleys on the next perpendicular joint. In other words, all the passing cables 78 on their respective idler pulleys of a particular joint must align smoothly onto the idler pulleys of a connecting joint.

For example, FIGS. 7 and 8 illustrate one embodiment to achieve smooth alignment. A first set of passing cables 78 are arranged on incrementally smaller idler pulleys to form a 45° imaginary line 132 on one side of the keying pulley. Likewise, a second set of passing cables 76 are symmetrically arranged on incrementally smaller idler pulleys about the joint's center to form a 45° imaginary line 130 on an opposite side of the keying pulley. As a result, the joint can be rotated at 90° increments and still align with the previous joint. Other angular increments can be achieved by positioning the passing cables in other configurations as long as all the passing cables on their respective idler pulleys of a particular joint are aligned smoothly onto the idler pulleys of a connecting joint.

DECOUPLED TENDON-DRIVEN WRIST

Figure 11:
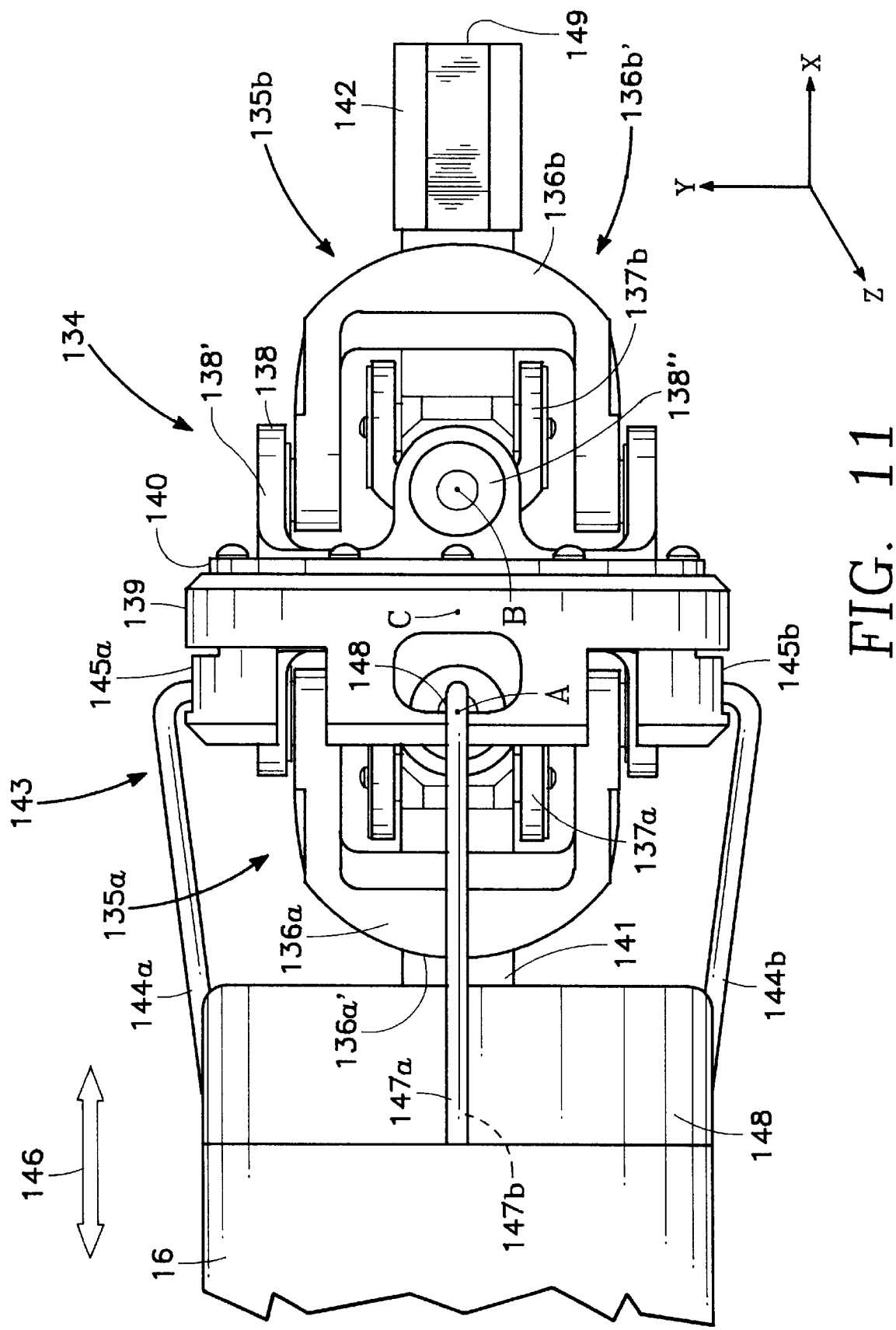
FIG. 11 illustrates one robot wrist of the present invention.

FIG. 11 illustrates one robot wrist of the present invention. In one embodiment of the present invention, the robot wrist 134 includes an input assembly 135A, an output assembly 135B, an inner housing 138, an outer housing 139, a middle housing 140, an input shaft 141, an output shaft 142, and a linkage assembly 143. The input and output assemblies 135A, 135B define a dual universal joint system that provides a three degree of freedom, singularity free, mechanically decoupled joint that operates in a full hemisphere of motion (up to 90 degrees in any direction).

The input assembly 135A includes an input outer universal 136A and an input inner universal 137A. Likewise, the output assembly 135B includes output outer and inner universals 136B, 137B which are counterparts of the input universals 136A, 137A. Each input universal 136A, 137A is symmetrical to its output universal 136B, 137B counterpart, respectively. The corresponding counterparts, defined by the symmetrical arrangement, are rotatably coupled to each other. The input and output universals are preferably coupled to each other by a tendon or cable arrangement (not shown) along a longitudinal axis parallel to an x axis.

Specifically, the universals are U-shaped and have arcuate faces on opposing input and output sides. The U-shaped configuration of the outer universals 136A, 136B define a respective slot for slidably receiving the input and output shafts 141, 142, respectively. Both outer and inner universals terminate in a pair of the arcuate faces. The arcuate faces have holes (not shown) for mounting the cables (not shown) between respective input and output outer universals 136A, 136B. Similarly, each inner universal 137B, 137B terminates in a pair of the arcuate faces. The inner universal faces also have holes (not shown) for mounting the cables (not shown) between respective input and output inner universals 137B, 137B. Thus, the input universals 136A, 136B rotate on the respective arcuate faces about the output universals 137B, 137B, to define an instantaneous center.

The tendon or cable coupling arrangement of each set of universals is functionally similar to the keying pulley/cable arrangement of FIGS. 4–8. For example, the input universals 136A, 137A are fixed to an input origin A and the output universals 136B, 137B are fixed to an output origin B. Each input and output origin, A, B, consist of two orthogonal axes about the y and z axes. A set of outer universal cables (not shown) couples the input outer universal 136A to the output outer universal 136B. Likewise, a set of inner universal cables (not shown) couples the input inner universal 137A to the output inner universal 137B. The outer universal set of cables is aligned perpendicularly to the inner universal set of cables. The outer and inner universal cables are preloaded (in accordance with the discussion below in FIG. 12) in order to eliminate backlash in the y and z axes. The outer and inner universal cables are preferably steel cables.

Also, each pair of coupled universals rotate with respect to one another about a defined instantaneous center, similar to the input and output keying pulley arrangement of FIGS. 4–8. However, the instantaneous center of FIG. 11 has two axes of rotation, namely the y and z axes, unlike the instantaneous center of FIGS. 4–8 which has only one axis or rotation. The rotational movements of the universals about their respective axes will be discussed below in detail.

The inner housing 138 has two halves, each being defined by two pairs of symmetrical crowns 138', 138". Each crown 138', 138" has four holes (not shown) centered on respective input and output origins A, B. The input universals 136A, 137A are rotatably mounted in the holes in each crown 138', 138" on the input origin A via bearings (not shown). The output universals 136B, 137B are rotatably mounted in the holes in each crown 138', 138" on the output origin B via bearings. When mounted in the inner housing 138, the input universals 136A, 137A rotate while constrained to the input origin A, and the output universals 136B, 137B rotate while constrained to the output origin B.

The output shaft 142 is rotatably coupled to the output inner universal 137B at the origin point B at the inner housing 138. The input shaft 141 is rotatably coupled to the input inner universal 136A at the input origin point A at the inner housing 138. This arrangement enables rotation of the input and output shafts 141, 142 about the y axis. The input and output shafts 141, 142 are coupled to the input and output inner universals 137A, 137B, respectively, with bearings (not shown). The inner universals 137A, 137B are rotatably coupled to the inner housing 138 at the z axis.

The output shaft 142 slides within the slot defined by the U-shaped configuration of the output outer universal 136B along the y axis. The input shaft 141 slides within the slot defined by the U-shaped configuration of the input outer universal 136A along y axis. This arrangement enables the input shaft 141 to rotate around the z axis and move the output inner universal 137B. Rotation of output shaft 142 around the y axis results in no movement of the output inner universal 137B. However, rotation of output shaft 142 around the y axis results in movement around the y axis of the output outer universal 136B.

The outer housing 139 is rotatably coupled to the middle housing 140 via a bearing assembly (not shown). The middle housing 140 is rotatably coupled to the inner housing 138 via a second bearing assembly (not shown). This enables rotation about the x axis between both the inner housing 138 and the middle housing 140 and the outer housing 139 and the middle housing 140. Thus, middle housing 140 rotates relative to inner housing 138 and outer housing 139.

The bearing assemblies are concentric and are nested inside one another. This concentric configuration allows both bearings to be assembled simultaneously, for easy assembly at any scale. Thus, the rotation of the input shaft 141 is transmitted through the housings and the universals to the output shaft 142 so that bidirectional rotation of the input shaft 141 results in bidirectional rotation of the output shaft 142. An actuator (not shown), which can be located in the forearm 16, rotates the input shaft 141 about the x axis (roll axis).

The linkage assembly 143 provides movement about the y and z axes of the output shaft 142 simultaneously. The linkage assembly 143 includes four links 144a, 144b, 147a, 147b, each having hooked ends (not shown). The links 144a, 144b are pivotally coupled about the y and z axes by a ball socket (not shown) at corresponding link attachments 145a, 145b, via the hooked ends. The link attachments 145a and 145b are rigidly attached to the middle housing 140. The links 147a and 147b are attached in a similar manner to the outer housing 139. Movement of the links 144a, 144b in the general direction of arrows 146 causes rotational movement of the inner housing 138 about the z axis of the wrist 134.

Movement of the links 147a, 147b in the general direction of arrows 146 results in rotational movement of the inner housing 138 about the y axis of the wrist 134. Any displacement of inner housing 138 relative to input shaft 141 is mirrored on output shaft 142 relative to inner housing 138.

Hence, there is a 2:1 amplification of movement of output shaft 142 over inner housing 138. This enables a full hemisphere of motion.

The links 144a, 144b, 147a, and 147b are confined to move in the x-y plane. Each link 144a, 144b, 147a, 147b is connected to a corresponding linear carriage (not shown). The linear carriages are located within the forearm 16 and are fully symmetrical. Each linear carriage moves the corresponding link attached to it in a back and forth direction as indicated by arrow 146. The linear carriages are coupled and actuated by actuators (not shown) located in the forearm 16 or base. The linear carriages include a 2:1 force multiplier that counteracts a 2:1 force divider inherent to the kinematics of the system. Inclusion of the 2:1 force multiplier increases the stiffness of the wrist 134 by a factor of four. Corresponding linear carriages actuate links 144a and 147a in opposition to links 144b and 147b in order to actuate the z and y axes, respectively. Also, the linkages inherently preload one another, thereby eliminating their source of backlash.

The wrist 134 provides movement about the x, y, and z axes simultaneously. The wrist 134 provides up to 180 degrees of motion about the y and z axes for the output shaft 142. The input shaft 141 is bidirectionally rotatable 360 degrees simultaneous with movement about the y and z axes. Thus, the work envelope of the wrist is a full hemisphere of motion.

An end cap 148 guides and positions the input shaft 141 and links 144a, 144b, 147a, 147b within the forearm 16. The input shaft 141 can be rotated inside the forearm within a ring bearing (not shown). The input shaft 141 can be coupled to a pulley assembly (not shown) within the forearm 16. This pulley assembly can be coupled to an actuator (not shown) located either within the forearm 16 or in the actuator base of FIG. 1. The actuator would transmit movement to the pulley assembly in order to move the input shaft 141.

The output shaft 142 has an end effector 149 for holding all types of tools (not shown). Circuitry can be routed through the arm to provide power to tools coupled to the end effector 149 that require electrical or pneumatic power. Also, the tendon or cable-driven arrangement (in accordance with the antibacklash scheme described below in detail) negates backlash in two of the three axes. In addition, the wrist 134 of the present invention has low stiction, high stiffness, and high strength-to-weight ratio.

For microsurgical applications, the wrist 134 can be approximately one inch in diameter, weigh approximately three ounces, and have a payload of about three inch-pounds. This allows the wrist 134 of the present invention to sustain a high work volume, while being lightweight, compact, and miniature in size.

Alternatively, in a preferred embodiment, the wrist 134 of FIG. 11 is modified to exclude components 136a, 136b, and 137b. Also, output shaft 142 is rigidly attached to housing 138 so that output shaft 142 cannot move relative to housing 138. In other words, output shaft 142 could be excluded and housing 138 extended so that housing 138 essentially becomes the output shaft.

By excluding the above mentioned components, the wrist 134 is transformed into a standard universal joint with dual bearing rings attached to the pitch and yaw actuation links. This arrangement provides decoupling of the pitch and yaw axes and allows the preferred wrist to have zero backlash in all axes. In addition, elimination of the aforementioned components provides zero backlash in the pitch, yaw, and roll axes and also provides greater efficiency, thereby reducing friction. Also, elimination of the aforementioned components reduces the work volume of the master robot by half.

Similar to the wrist 134 discussed above, the actuation links of the preferred wrist are activated by the tendons, which are passed through the elbow and shoulder joints to the base. Likewise, the roll is activated by tendons which rotate the universal joint, passing rolling motion to a face plate located at the end of the wrist. The face plate allows for attachment of various components, such as variations of the stylus 13 shown in FIG. 1, depending on the application. Also, similar to the tendons controlling the pitch and yaw axes, the tendons controlling the roll axis pass through the elbow and shoulder joints, and exit the base housing.

Figure 13:
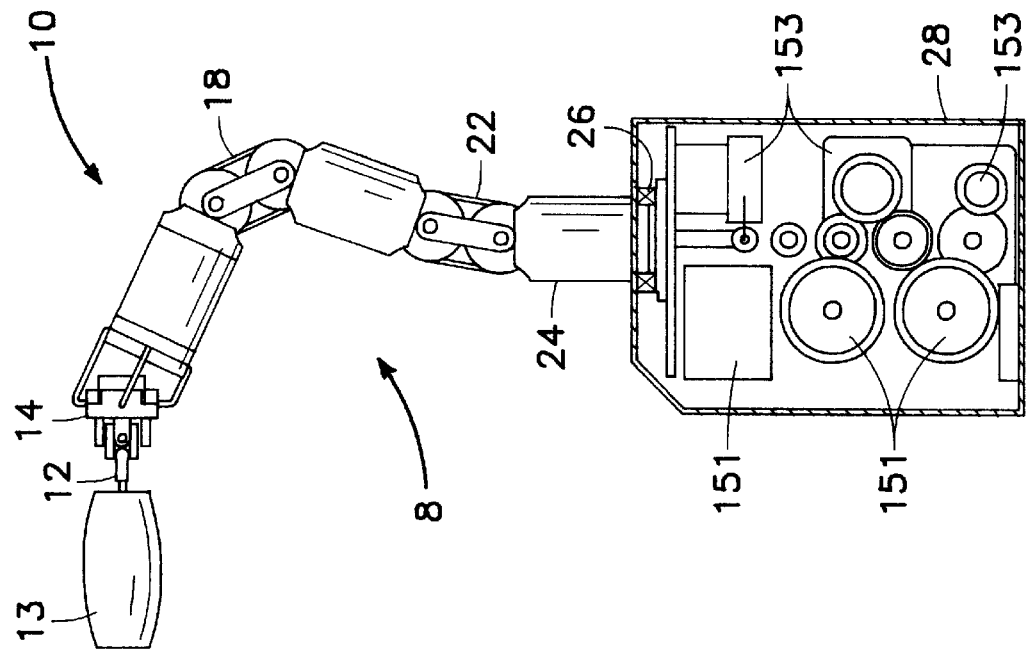
FIG. 13 illustrates a left side cut-away view of the base of the robot manipulator of the present invention.
Figure 12:
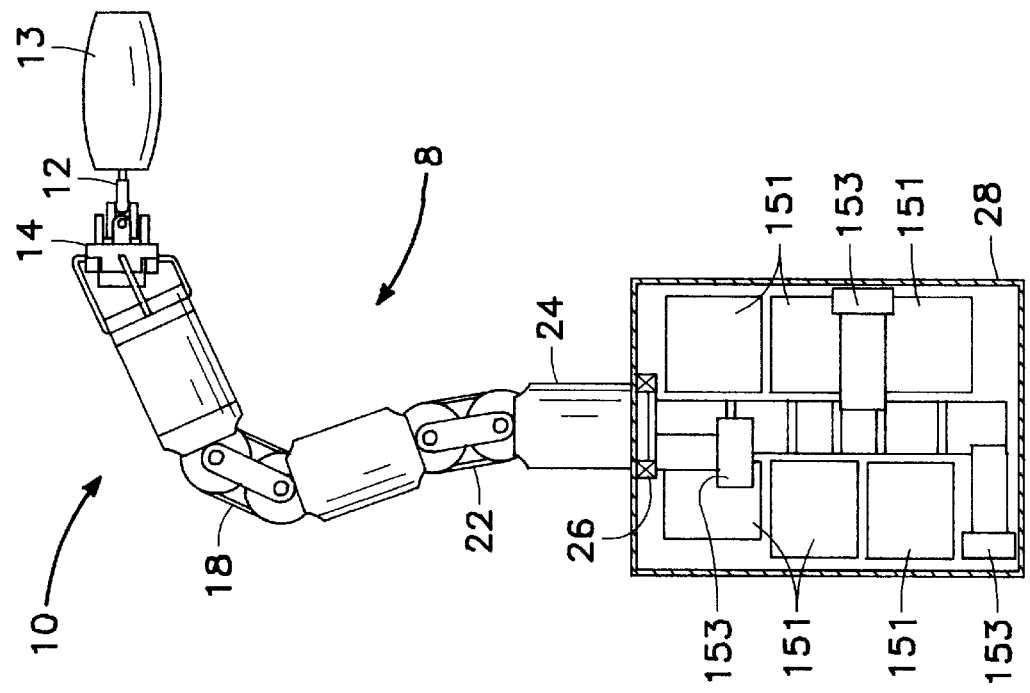
FIG. 12 illustrates a front cut-away view of the base of the robot manipulator of the present invention.

FIG. 12 illustrates a front cut-away view of the base of the robot manipulator of the present invention and FIG. 13 illustrates a left side cut-away view of the base of the robot manipulator of the present invention. The base 28 houses components that control the arm. The arm 10 is mounted to the actuator base 28 which can be a cylindrical base housing.

For microsurgical applications, the base housing is preferably about 23 cm long, 18 cm wide, and 10 cm high. The tendons passing through the arm 10 of FIGS. 4–8 enter the base 28 through a connection between the arm 10 and the base 28. The tendons are wound on five independent tendon spools (not shown), one for each axis (the shoulder 22 axis, the elbow 18 axis, and the pitch, yaw, and roll axes of the wrist 14). The torso 26 rotates relative to the base 28 about a sixth axis and is driven by gears (not shown).

In order to decouple the five axes from the sixth axis (torso), the tendons of the other five axes are twisted about their length along the sixth axis. Although this arrangement of the present invention produces decoupling, it does vary the tension in the tendons by a small percentage (<1%). Also, as a result, travel of the sixth axis is restricted to approximately 30 degrees. However, since the input device 8 has indexing capabilities, a high range of motion is not necessary.

Each of the six axes is equipped with a high-resolution optical encoder 151 (for a total of six encoders), such as an encoder capable of 40,000 counts per revolution. The six encoders 151 are housed in the base 28 and are necessary for reducing the amount of gearing necessary to achieve the required positional resolution while limiting friction.

The encoders 151 are attached to the tendon spools and the torso axis via a standard single stage antibacklash geartrain. Alternatively, the antibacklash geartrain described in FIGS. 14–15 may be utilized. In the preferred embodiment, geartrain ratios vary from about 1.25:1 on the torso 26, shoulder 22, and elbow joints 18 to as high as about 5.3:1 on the roll axis.

In addition, the base 28 also includes three arm motors 153 and three wrist motors (not shown) to create the force-feedback capability on the torso 26, shoulder 22, and elbow axes 18, and the three-axis wrist 14, respectively. The force feedback can be applied to the input deivce 8 for providing feedback to an operator of the input device 8. The force feedback can be generated from the slave robot (see FIG. 16) which the input device 8 controls. Also, the force feedback can be generated from an external device, such as a programmed processor, to produce fictitious forces on the input device. The fictitious forces can represent desired boundaries to constrain the slave robot within.

With the aforementioned arrangement, the input device 8 can produce approximately six ounces of force, and may be driven to produce approximately 13 Newtons force and about 300 N-mm of torque at the wrist. Minimizing the force output minimizes the friction and reflected inertia for a given motor. The motors are preferably DC brushless motors, but could be replaced with any other type of motor. These motors are attached to the tendon spools via a standard single stage spur geartrain. Also included in the base 28 is the electrical wiring (not shown) to support the motors and encoders 151, all of which are connected to electrical connectors (not shown) at the rear of the housing for electrical interface with an external source (not shown).

Thus, the input device 8 has 6-axes of positional input with the capacity to produce 6-axes force-feedback. The drive motors create the force-feedback capability on the torso 26, shoulder 22, and elbow 18 axes. Also, the plurality of high-resolution optical encoders 151 reduce the amount of gearing necessary to achieve the required positional resolution while limiting friction.

The total work volume of the input device 8 is determined by the independent joint limits described above, primarily constrained by that of the torso 26 (with the aforementioned arrangement, the torso has a range of motion of approximately 30 degrees). This results in a wedge-shaped work volume, with the apex aligned with the torso axis. The positional accuracy is maintained over the entire volume.

ANTIBACKLASH MECHANISM

Figure 15:
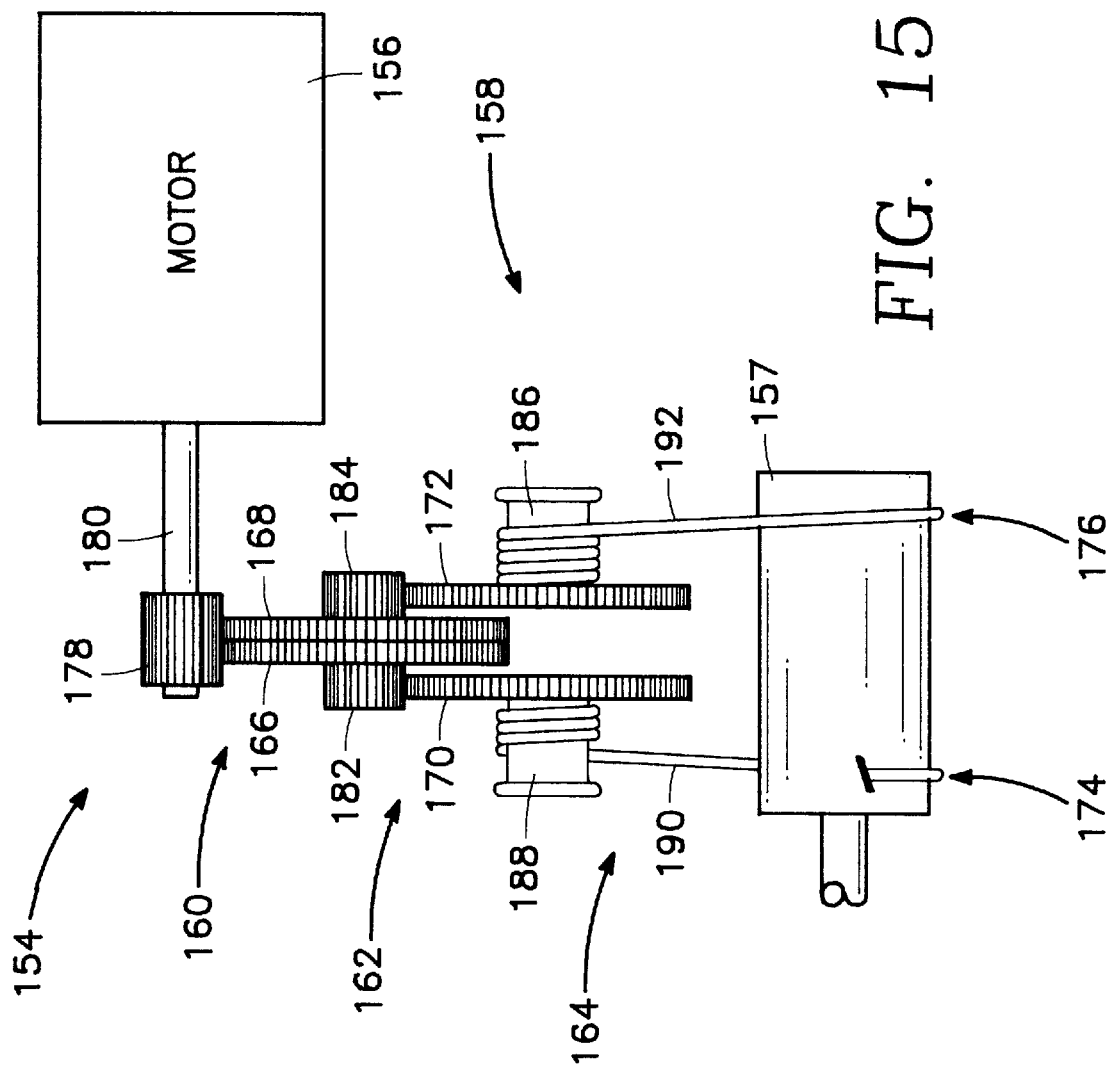
FIG. 15 illustrates a front view of one antibacklash mechanism that can be used in accordance with the present invention.
Figure 14:
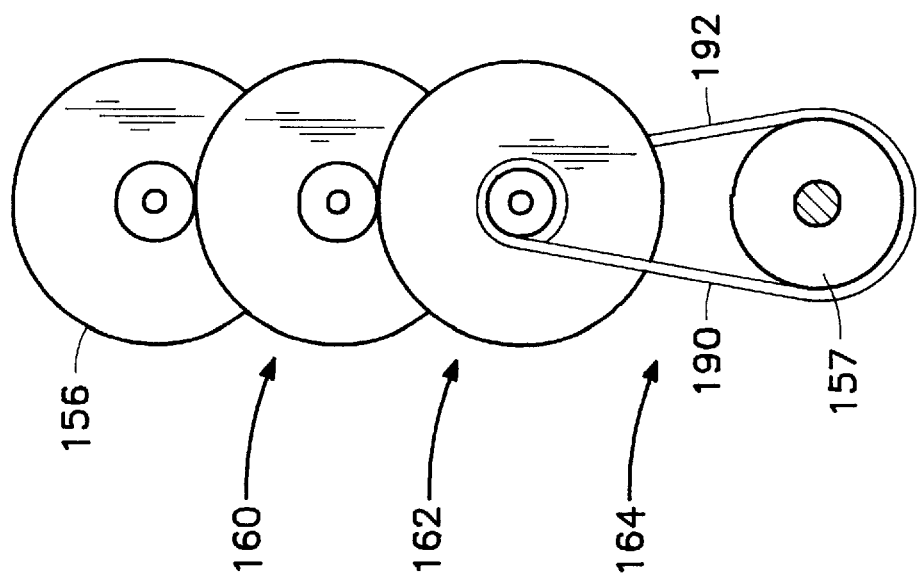
FIG. 14 illustrates a side view of one antibacklash mechanism that can be used in accordance with the present invention.

The input device 8 utilizes a standard single stage antibacklash mechanism. Alternatively, FIGS. 14–15 illustrate an alternative antibacklash mechanism of the present invention incorporated in the actuator base 28 of FIG. 1. The alternative antibacklash mechanism 154 can be used with the joints of FIGS. 2–11 to overcome the problems of conventional antibacklash schemes. The antibacklash mechanism of the present invention is incorporated in the robot manipulator between the actuators 156, such as motors at the actuator base, and an output 157 or the device to be actuated, such as the output link 62 of FIG. 5 of a particular joint.

The antibacklash mechanism 154 is a multiple stage device not limited to any particular number of stages. The antibacklash mechanism 154 utilizes a drivetrain system 158 with drive components such as gears, belts, and/or cables. FIGS. 14–15 illustrate the antibacklash mechanism 154 having three stages 160, 162, and 164 with a pair of gears 166 and 168 and 170 and 172 at the first 160 and second stages 162, respectively.

Two independent transmission paths, defined by the gears 166, 182, 170, and 168, 184, 172, are formed as two identical geartrains in parallel for each drive. For example, a given joint's motor 156 would have one spur pinion 178 on its shaft 180 which would engage with two independent gears 166 and 168 of the first stage 160. The two independent transmission paths are mechanically coupled only at an input, such as the motor 156, and an output, such as an actuation pulley located on a particular joint.

The first and second stage gears 166 and 168 are free to rotate independent of each other, respectively. The pinion 178 on the motor 156 at the input drives both of the independent first stage gears 166 and 168 to complete a first stage 160 reduction. Two second stage 162 pinions 182 and 184 are rigidly attached to each of the first stage gears 166 and 168, for example on a gear shaft. The two second stage 162 pinions 182 and 184 drive the two independent second stage gears 170 and 172, thus completing the second stage 162 reduction (additional gear stages can be used).

Each of the second stage gears 170 and 172 drives an independent actuation drum or tendon spool 186 and 188 on a common shaft. Two cables 190 and 192, each attached to one of the spools 188 and 186, terminate on the output, which can be for example the actuation pulleys 106 and 108 of FIGS. 4–11. The cables 190 and 192 actuate the particular joint, thereby completing the third stage 164 and completing a dual drive system 174 and 176. Thus, with this arrangement, the only common points between the dual drive system 174 and 176 are at an origination at the input 156 (i.e. the motor 156) and the termination at the output 157 (i.e. the actuation pulleys 106 and 108 at the joint).

This dual drive arrangement allows for cable tensioning, eliminates backlash, and maximizes mechanical efficiency. Hence, from this feature, one of the advantages of the antibacklash mechanism of the present invention is convenient preloading of the gear stages 160, 162, and 164 to eliminate backlash. The dual drivetrain system is preloaded by first disengaging the motor 156 from the first stage 160 gears 166 and 168 so that the two gears 166 and 168 can be counter-rotated relative to one another. This counter-relation preloads the cables 190 and 192 to the desired tension. This rotation passes from stage to stage until all the cables become tensioned. When the desired preload tension is achieved, the motor 156 is simply re-engaged and the preload is locked.

Also, by disengaging the motor 156, the two drivetrains 174 and 176 can be reloaded relative to one another if necessary. In addition, since the preload is passed from one stage to the next stage, the value of the preload is proportional to any gear ratios between the stages 160, 162, and 164. Moreover, an optimum preload is achieved automatically in all the stages 160, 162, and 164 simultaneously because the preloading is passed via the gearing from the input motor 156 to the output 157. This preload is transmitted throughout the entire dual drivetrains 174 and 176, thereby eliminating backlash in all drivetrains. Further, the preload is transmitted proportionately to the gear ratio for each stage, to optimize the preload for maximum mechanical efficiency, unlike the prior art where each stage is independently preloaded.

Thus, the alternate antibacklash mechanism 154 of the present invention provides geartrains with zero backlash, convenient preload adjustment, preload adjustment of all stages simultaneously, and stage preload proportional to stage ratio to achieve maximum mechanical efficiency. Also, since the required gear ratio for the microsurgical robot manipulator described above is between the actuator and each joint, the antibacklash mechanism of FIGS. 14–15 is global for all the joints and encompasses a wide range of ratios. In addition, for the cable-driven robot manipulator, the cable preload is adjustable to accommodate stretching over time.

DETAILED COMPONENTS OF THE MICROSURGICAL ROBOT MANIPULATOR

Figure 16:
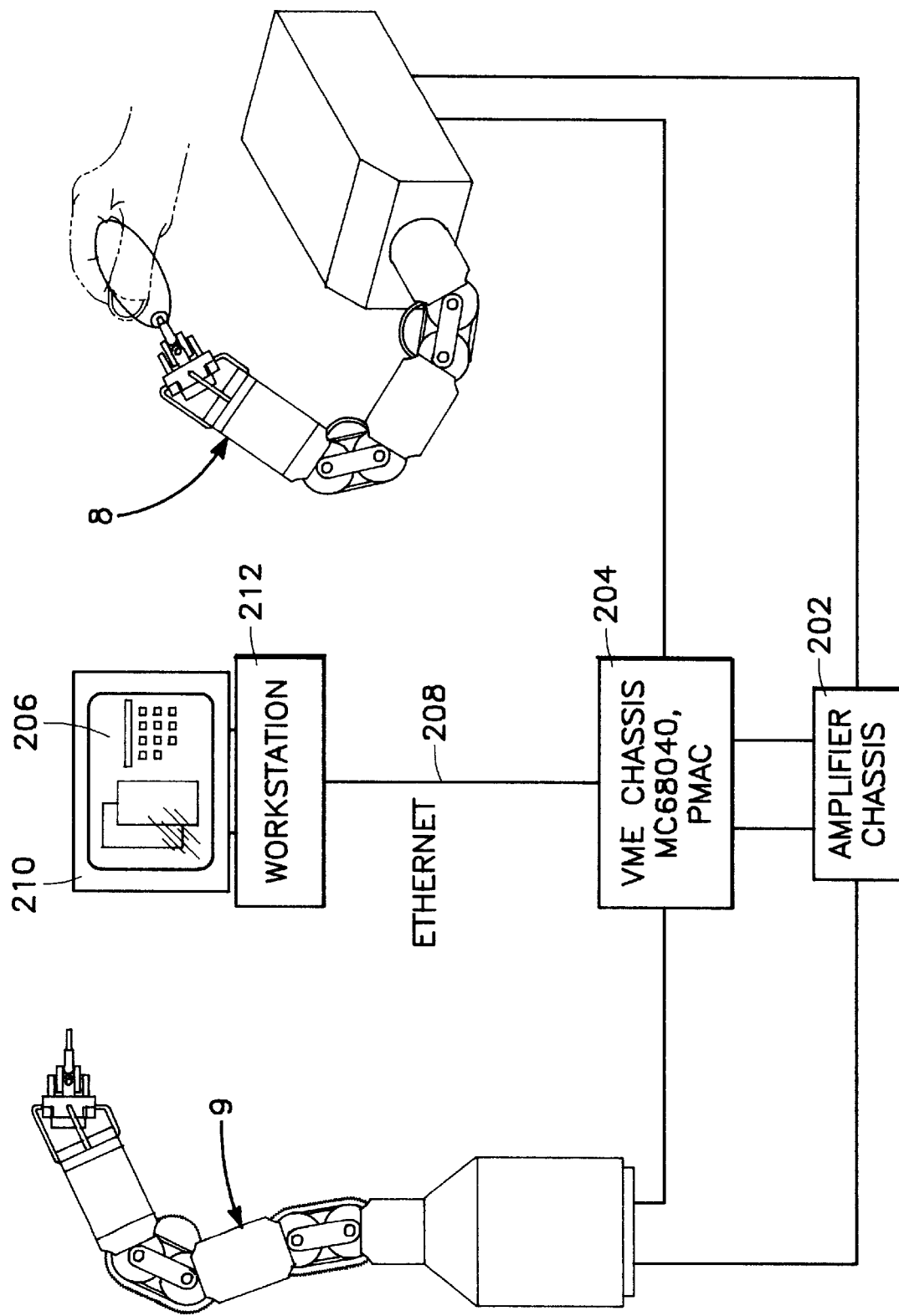
FIG. 16 illustrates an overview of the interaction between the sub-systems of the robot manipulator of the present invention.

FIG. 16 illustrates an overview of the interaction between the sub-systems of the robot manipulator of the present invention. The input device 8 functions as a master robot manipulator in a microsurgical teleoperated robot system. The overall system architecture includes a slave robot manipulator 9 coupled to an amplifier chassis 202. The amplifier chassis 202 is coupled to a control chassis 204, such as a VME chassis, which is coupled to a workstation 206, such as a UNIX workstation via standard twisted pair Ethernet 208. The workstation has a graphical user interface 210 which can have a keyboard or other input device 212 for ease of control by a user. Also, the amplifier chassis 202 is coupled to the motors of the master robot manipulator 8 and the control chassis 204 is coupled to the encoders 151 of the master robot manipulator 8.

A force feedback can be applied to the input deivce 8 and can be generated from the slave robot 9. This would enable a user to operate the slave robot 9 via the input device 8 without physically viewing the slave robot 9. Also, the force feedback can be generated from the workstation to represent fictitious forces. These fictitious forces are very desirable because they can constrain the input device's 8 control of the slave robot 9 to be within imaginary predetermined boundaries.

In summary, with the aforementioned arrangement, very low inertia, very low frictional aspects, and zero backlash in the axes of the wrist are achieved. In addition, since the master robot has indexing capabilities, a high range of motion is not necessary.

What is claimed is:

1. A robot manipulator coupled to an external device, said robot manipulator comprising:

an actuator base with plural actuators and having a mechanism for receiving forces generated by said external device;

an end effector interactive with an operator;

a force feedback sensor coupled between said end effector and said actuator base for receiving said forces from said actuator base, converting said forces into feedback forces, and providing said feedback forces to said operator;

plural arms extending seriatim between said end effector and said actuator base; and plural joints connected between pairs of adjacent arms;

wherein each one of said plural joints comprises a coupling device for mechanically coupling respective ones of said actuators to respective ones of said joints through intermediate ones of said joints, and wherein said coupling device is decoupled from said intermediate joints.

2. The invention as set forth in claim 1, wherein said external device is an output robot manipulator.

3. The invention as set forth in claim 1, wherein said external device is a programmed processor for producing fictitious forces.

4. The invention as set forth in claim 3, wherein said coupling device comprises:

a first keying drive component coupled to a second keying drive component;

a first passing drive component coupled to respective ones of said actuators for receiving rotational motion; and a second passing drive component coupled to said first passing drive component for receiving said rotational motion from said first passing drive component and for transmitting said received rotational motion to one of said plural joints;

wherein said first and second keying drive components are constrained to rotate about one another to define an instantaneous center of rotation;

wherein said first passing drive component rotates with respect to said second passing drive component about said instantaneous center of rotation.

5. The invention as set forth in claim 4, wherein said first keying drive component is a first keying pulley and said second keying drive component is a second keying pulley.

6. The invention as set forth in claim 5, further comprising plural keying cables for rotatably coupling said first keying pulley to said second keying pulley and for rotationally constraining said first keying pulley to said second keying pulley so that said first and second keying pulleys rotate with respect to one another about said instantaneous center of rotation.

7. The invention as set forth in claim 4, wherein said first and second keying drive components are keying spur gears.

8. The invention as set forth in claim 4, wherein said first and second passing drive components are passing spur gears.

9. The invention as set forth in claim 4, wherein said first passing drive component is a first passing pulley and said second passing drive component is a second passing pulley.

10. The invention as set forth in claim 9, further comprising plural passing cables for rotatably coupling said first passing pulley to said second passing pulley and for rotationally constraining said first passing pulley to said second passing pulley so that said first and second passing pulleys rotate with respect to one another about said instantaneous center of rotation.

11. The invention as set forth in claim 3, wherein all actuators drives of said manipulator are located within said actuator base.

12. The invention as set forth in claim 3, wherein each of said joints comprises dual independent antibacklash drive transmission preloaded with respect to one another.

13. The invention as set forth in claim 3, wherein said plural joints further comprises an antibacklash mechanism for transmitting motion without backlash from respective ones of said plural actuator drives to respective ones of said joints, said antibacklash mechanism comprising:

at least a first transmission stage comprising first dual drive components, wherein both of said first dual drive components are rotatably coupled to said respective ones of said plural actuator drives and are independently rotatable with respect to one another; and at least a second transmission stage comprising a second dual drive reduction mechanism, wherein each one of said second dual drive reduction mechanism is rigidly attached to one of said first dual drive components and is rotatably coupled to said respective ones of said joints, so that rotational motion of said respective ones of said plural actuator drives is transmitted through said first and second stages, to said respective ones of said joints without backlash.

14. The invention as set forth in claim 1, further comprising a universal joint coupled to said end effector.

15. The invention as set forth in claim 14, wherein said universal joint includes dual bearing rings attached to pitch and yaw actuation links to provide decoupling of said pitch and yaw actuation links and zero backlash in all axes.

16. A robot manipulator coupled to an external device, said robot manipulator comprising:

an actuator base with plural actuators and having a mechanism for receiving forces generated by said external device;

an end effector interactive with an operator;

a force feedback sensor coupled between said end effector and said actuator base for receiving said forces from said actuator base, converting said forces into feedback forces, and providing said feedback forces to said operator; and a plurality of joints each coupled to said actuators, wherein each one of said joints comprises, an input link having at least an input keying drive component rotatable on an input axis, an output link coupled to said input link and having at least an output keying drive component rotatable on an output axis, wherein said input and output keying drive components are constrained to rotate about one another to define an instantaneous center of rotation, at least an input passing drive component rotatable on said input link and coupled to said actuator for receiving rotational motion, and at least an output passing drive component rotatable on said output link and coupled to said input passing drive component for receiving said rotational motion decoupled from said one joint.

17. The invention as set forth in claim 16, wherein said input passing drive component rotates with respect to said output passing drive component about said instantaneous center of rotation.

18. The invention as set forth in claim 16, wherein said input keying drive component is an input keying pulley and said output keying drive component is an output keying pulley.

19. The invention as set forth in claim 18, further comprising plural keying cables for rotatably coupling said input keying pulley to said output keying pulley and for rotationally constraining said input keying pulley to said output keying pulley so that said input and output keying pulleys rotate with respect to one another about said instantaneous center of rotation.

20. The invention as set forth in claim 16, wherein said input and output keying drive components are keying spur gears.

21. The invention as set forth in claim 16, wherein said input and output passing drive components are passing spur gears.

22. The invention as set forth in claim 16, wherein said input passing drive component is an input passing pulley and said output passing drive component is an output passing pulley.

23. The invention as set forth in claim 22, further comprising plural passing cables for rotatably coupling said input passing pulley to said output passing pulley and for rotationally constraining said input passing pulley to said output passing pulley so that said input and output passing pulleys rotate with respect to one another about said instantaneous center of rotation.

24. The invention as set forth in claim 16, wherein said input and output links are coupled to each other by hinged side struts.

25. The invention as set forth in claim 16, wherein said input link further comprises plural input idler pulleys and said output link further comprises corresponding plural output idler pulleys, wherein each corresponding pair of said input and output idler pulleys drives one of said joints.

26. A robot manipulator coupled to an external device, said robot manipulator comprising:

an actuator base with plural actuators and having a mechanism for receiving forces generated by said external device;

an end effector interactive with an operator;

a force feedback sensor coupled between said end effector and said actuator base for receiving said forces from said actuator base, converting said forces into feedback forces, and providing said feedback forces to said operator; and a plurality of joints each coupled to said actuators, wherein each one of said joints comprises, an input link having an input keying pulley, an output link coupled to said input link and having an output keying pulley, a keying cable for rotatably coupling said input keying pulley to said output keying pulley, wherein said input and output keying pulleys are constrained to rotate about one another thereby defining an instantaneous center of rotation, at least one input idler pulley rotatable on said input link and coupled to said actuator for receiving rotational motion, at least one output idler pulley rotatable on said output link, and at least one passing cable coupled to each input and output idler pulley for transmitting rotational motion of said input idler pulley and said output idler pulley decoupled from said one joint.

27. The invention as set forth in claim 26, wherein said input idler puller rotates with respect to said output idler pulley about said instantaneous center of rotation.

28. The invention as set forth in claim 26, wherein said input and output links are coupled to each other by hinged side struts.

29. The invention as set forth in claim 26, wherein said input and output links are displaced by at least a diameter of each of said input and output links to facilitate 180 degree rotation.

30. The invention as set forth in claim 26, wherein rotation of each of said joint is dependant upon a diameter ratio between said input and output keying pulleys.

31. The invention as set forth in claim 26, wherein all of said keying pulleys have the same diameter.

32. The invention as set forth in claim 26, wherein said input link further comprises plural input keying pulleys and said output link further comprises plural output keying pulleys.

* * * * *